US00PP31816P2

(12) United States Plant Patent
Ammerlaan

(10) Patent No.: US PP31,816 P2
(45) Date of Patent: May 26, 2020

(54) ***CRASSULA* PLANT NAMED 'OVWOODS01'**

(50) Latin Name: ***Crassula arborescens* subsp. *undilatifolia***
Varietal Denomination: OVWOODS01

(71) Applicant: Ovata B.V., Bleiswijk (NL)

(72) Inventor: Johannes Hendrikus Adrianus Ammerlaan, Bleiswijk (NL)

(73) Assignee: Ovata B.V., Bleiswijk (NL)

( * ) Notice: Subject to any disclaimer, the term of this patent is extended or adjusted under 35 U.S.C. 154(b) by 0 days.

(21) Appl. No.: 16/501,541

(22) Filed: Apr. 26, 2019

(51) Int. Cl.
*A01H 5/00* (2018.01)

(52) U.S. Cl.
USPC ..... Plt./373

(58) Field of Classification Search
USPC ..... Plt./373
CPC ..... A01H 5/00
See application file for complete search history.

*Primary Examiner* — Annette H Para
(74) *Attorney, Agent, or Firm* — Samuel R. McCoy, Jr.

(57) ABSTRACT

A new and distinct variety of *Crassula* plant named 'OVWOODS01' which is characterized by the combination of a broad spreading to upright and freely-branching growth habit, glaucous variegated stems, an abundance of glaucous variegated foliage which is narrowly margined dark red, and the stability of all characteristics from generation to generation.

2 Drawing Sheets

Latin name of the genus and species: The Latin name of the genus and species of the novel variety disclosed herein is *Crassula arborescens* subsp. *undilatifolia.*

Variety denomination: The inventive variety of *Crassula* disclosed herein has been given the variety denomination 'OVWOODS01'.

BACKGROUND OF THE INVENTION

Parentage: 'OVWOODS01' originated as a naturally occurring, whole-plant mutation of *Crassula* 'OVCRAS03' (Community Plant Variety Rights grant number 46259), a variety developed and owned by the inventor. The inventor of 'OVWOODS01' is a commercial ornamental plant producer and regularly discovers mutations of *Crassula* at his greenhouse operation in Bleiswijk, The Netherlands. For said mutations which seem to exhibit commercial potential, cuttings are taken to produce trial plants which are subsequently grown for evaluation.

The variety now called 'OVWOODS01' was initially discovered in the summer of 2016 as a whole-plant mutation of 'OVCRAS03' which exhibited variegated stems, branches and foliage. At the time of discovery, cuttings were taken and the resulting plants were evaluated at the inventor's greenhouse. After further evaluation it was determined that the candidate's variegated foliage would prove favorable for commercial marketability. The new variety was given the breeder denomination 'OVWOODS01'.

Asexual Reproduction: The variety now called 'OVWOODS01' was first asexually propagated by stem cuttings in the summer of 2016 at a greenhouse in Bleiswijk, The Netherlands and has since been vegetatively propagated through four additional generations. Through subsequent generations, the unique features of this cultivar are stable and reproduced true to type.

SUMMARY OF THE INVENTION

The cultivar 'OVWOODS01' has not been observed under all possible environmental conditions and the phenotype may vary somewhat with variations in environment such as temperature, day length, and light intensity, without, however, any variance in genotype. The following traits have been repeatedly observed and are determined to be the unique characteristics of 'OVWOODS01'. These characteristics in combination distinguish 'OVWOODS01' as a new and distinct *Crassula* cultivar:

1. *Crassula* 'OVWOODS01' exhibits a freely branching, broad spreading to upright growth habit; and
2. *Crassula* 'OVWOODS01' exhibits green-white and green variegated stems and branches; and
3. *Crassula* 'OVWOODS01' exhibits glaucous stems and branches which are covered with greyed-green epicuticular wax; and
4. *Crassula* 'OVWOODS01' exhibits foliage which is marbled and striped with a mixture of green, yellow-green and greyed-green; and
5. *Crassula* 'OVWOODS01' exhibits foliage which is broadly margined white to yellow-white; and
6. *Crassula* 'OVWOODS01' exhibits distal foliage margins which are narrowly colored greyed-purple; and
7. *Crassula* 'OVWOODS01' exhibits glaucous foliage which is covered with greyed-green epicuticular wax.

BOTANICAL DESCRIPTION OF THE PLANT

Figure 1:
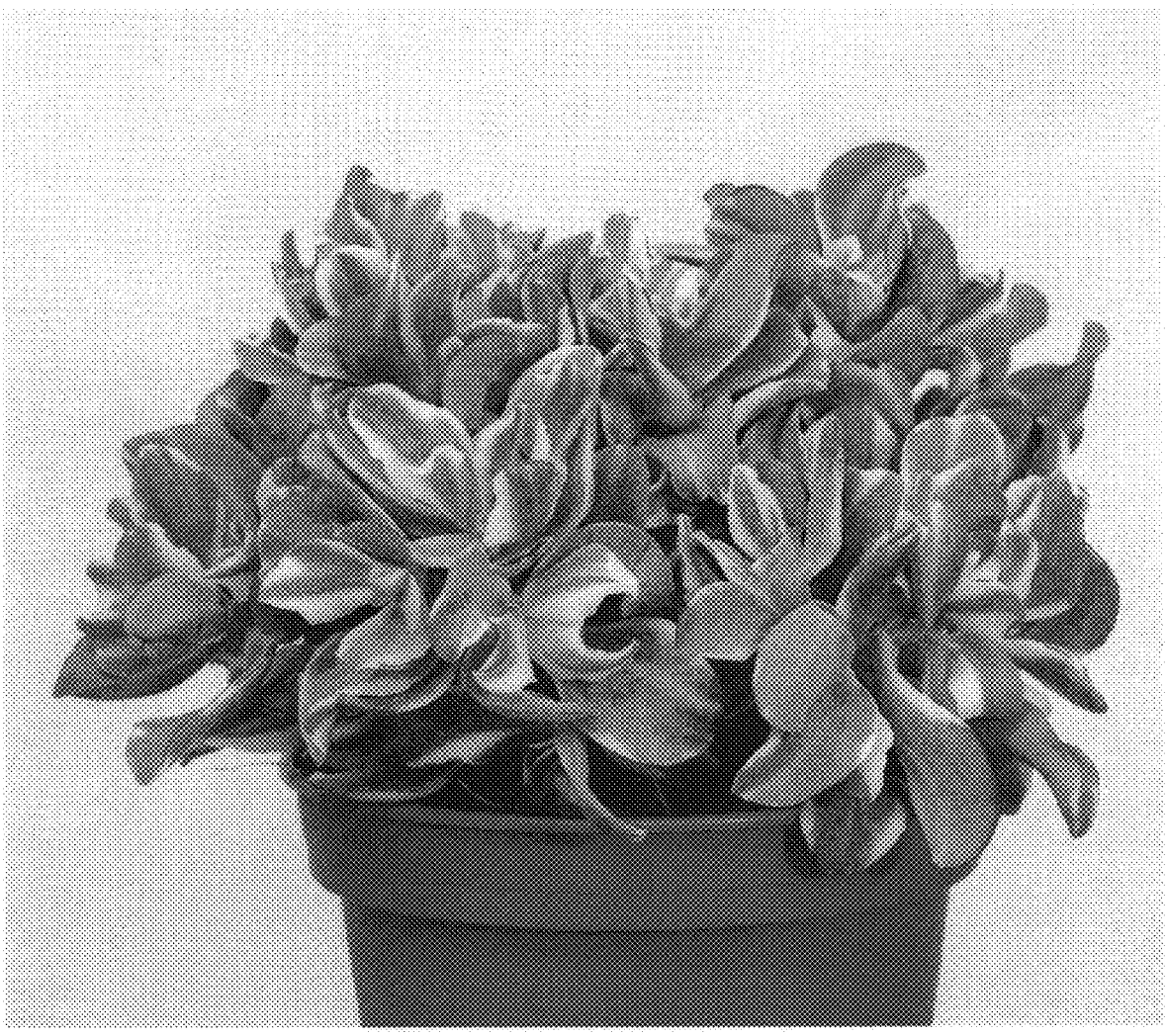
FIG. 1 illustrates, as nearly true as it is reasonably possible to make the same in color photographs of this type, an exemplary plant of 'OVWOODS01' grown in a commercial greenhouse in Heerhugowaard, The Netherlands. This plant is approximately 12 months old, shown planted in a 12 cm container.
Figure 2:
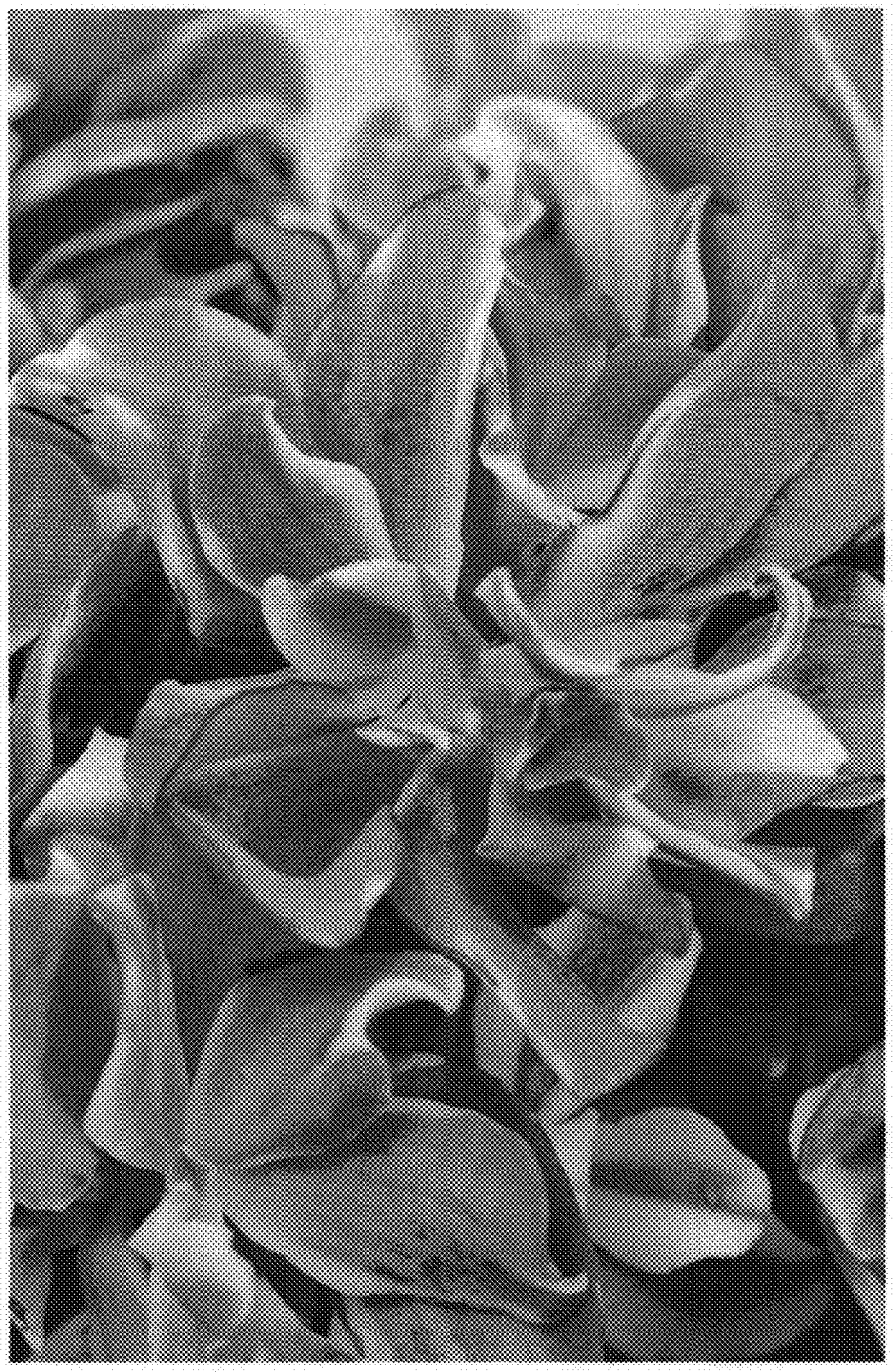
FIG. 2 illustrates, as nearly true as it is reasonably possible to make the same in color photographs of this type, the typical foliage of 'OVWOODS01'.

The following observations and measurements made in November of 2018 describe averages from a sample set of six specimens of 12 month-old 'OVWOODS01' plants grown in 12 cm nursery containers at commercial greenhouse in Bleiswijk, The Netherlands. The plants were grown in full sun to semi-shade. Plants were maintained with a standard fertility program for plants of this type and regularly watered with overhead irrigation as well as through use of ebb-and-flow hydroponic greenhouse benches. No chemical pest measures were taken.

Those skilled in the art will appreciate that certain characteristics will vary with older or, conversely, with younger plants. 'OVWOODS01' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2015 (sixth edition).

A botanical description of 'OVWOODS01' and comparisons with the parent and closest known commercial comparator are provided below.

Plant description:

*Growth habit*.—Broad spreading to upright perennial.

*Plant form*.—Irregular flattened globular.

*Average height*.—13.8 cm from the soil level to the top of the foliar plane.

*Plant spread*.—Average of 22.1 cm.

*Growth rate*.—Low to moderate.

*Plant vigor*.—Moderate.

*Propagation type*.—Stem cuttings.

*Time to initiate roots*.—Approximately 14 days to initiate roots at temperatures ranging from 15 to 20 degrees Celsius.

*Time to produce a rooted cutting*.—Approximately 6 weeks to produce a rooted cutting.

*Disease resistance*.—Neither resistance nor susceptibility to typical *Crassula* pests and diseases has been observed.

*Environmental tolerances*.—Adapt to, at least, USDA Zones 10 and 12 and temperatures as high as 40 degrees Celsius; low tolerance to rain; moderate to high tolerance to wind.

Root system:

*General*.—Moderately dense and freely branched rooting; roots are moderately fibrous.

*Distribution in the soil profile*.—Shallow to moderately deep.

*Diameter of roots*.—0.8 mm on average.

*Texture*.—Smooth and glabrous.

*Color*.—Greyed-orange, nearest to RHS 164B.

Stem:

*General branching habit*.—Basally branching main stems; freely branching with lateral branches. Pinching isn't required but will improve branching.

*Main stems*.—Quantity of main stems per plant — 2. Attitude — Upright and outward. Cross-section — Rounded. Texture — Glabrous; glaucous. Luster — Matte. Strength — Strong. Color, juvenile — Axially variegated green and in between yellow-green to white, nearest to RHS 1443C and 150D to 155B but closest to 155B; epicuticular wax covering the surface is greyed-green, nearest to RHS 190B. Color, mature — Green-white, nearest to in between RHS 157B and 157C, and axially striped green, nearest to in between 137C and 137D; epicuticular wax covering the surface is greyed-green, nearest to RHS 190B. Color at internodes — Green-white, nearest to in between RHS 157B and 157C, and axially striped green, nearest to in between 137C and 137D; epicuticular wax covering the surface is greyed-green, nearest to RHS 190B. Color of the oldest wood — Greyed-yellow, nearest to in between RHS 161B and 161C, and axially striped yellow-green, nearest to in between RHS 146B and 146C.

*Lateral branches*.—Quantity of lateral branches — 9. Length of lateral branches — Approximately 6.7 cm. Diameter of lateral branches — Approximately 0.75 cm. Internode length — Approximately 1.0 cm. Attitude — At an average angle of 65 degrees to vertical, varying between 45 and 85 degrees. Cross-section — Rounded. Texture — Glabrous; glaucous. Luster — Matte. Strength — Strong. Color, juvenile — Axially variegated green and in between yellow-green to white, nearest to RHS 1443C and 150D to 155B but closest to 155B; epicuticular wax covering the surface is greyed-green, nearest to RHS 190B. Color, mature — Green-white, nearest to in between RHS 157B and 157C, and axially striped green, nearest to in between 137C and 137D; epicuticular wax covering the surface is greyed-green, nearest to RHS 190B. Color at internodes — Green-white, nearest to in between RHS 157B and 157C, and axially striped green, nearest to in between 137C and 137D; epicuticular wax covering the surface is greyed-green, nearest to RHS 190B.

Foliage:

*Arrangement*.—Opposite.

*Division*.—Simple.

*Quantity*.—14 per lateral branch.

*Attitude*.—Upward.

*Lamina*.—Shape — Obovate. Aspect — Concave, moderately axially twisted, and reflexed. Dimensions — 4.9 cm long and 2.9 cm wide. Thickness — Approximately 0.3 cm. Apex — Obtuse to bluntly acute. Base — Cuneate. Margin — Slightly textured with very small bumps and incisions; strongly coarsely undulate. Pubescence, texture and luster of the adaxial surface — Glabrous, smooth, and slightly glossy; moderately to heavily glaucous. Pubescence, texture and luster of the abaxial surface — Glabrous, smooth, and very slightly glossy; moderately to heavily glaucous. Color — Juvenile foliage, adaxial surface — Marbled and striped with a mixture of green and greyed-green, RHS NN137B, NN137C, 138A, 190A, 191A and 191B; broadly to very broadly margined yellow to greyed-yellow, RHS 8C, 8D, 160C, and 160D; distal margins are narrowly colored greyed-red, nearest to RHS 180D; the epicuticular wax covering the leaf surface is greyed-green, nearest to in between RHS N189C and N189D. Juvenile foliage, abaxial surface — Marbled and striped with a mixture of green and greyed-green, RHS NN137B, NN137C, 138A, 190A, 191A and 191B; broadly to very broadly margined yellow to greyed-yellow, RHS 8C, 8D, 160C, and 160D; distal margins are narrowly colored greyed-red, nearest to RHS 180D; the epicuticular wax covering the leaf surface is greyed-green, nearest to RHS 191B. Mature foliage, adaxial surface — Marbled and striped with a mixture of green, yellow-green and greyed-green, RHS NN137A, NN137B, NN137C, 143A, 146B, N189C and N189D; broadly margined white to yellow-white, RHS 155A, 155B, and 158D; distal margins are narrowly colored greyed-purple, nearest to RHS 186A; the epicuticular wax covering the leaf surface is greyed-green, nearest to in between RHS N189C and N189D. Mature foliage, abaxial surface — Marbled and striped with a mixture of green, yellow-green and greyed-green, RHS NN137C, 146B, N189C and N189D; broadly margined white to yellow-white, RHS 155A, 155B, and 158D; distal margins are narrowly colored greyed-purple, nearest to RHS 186A; the epicuticular wax covering the leaf surface is greyed-green, nearest to RHS 191B. Venation — No veins are visible.

*Petiole*.—No petioles present, leaves sessile.

Inflorescence: No flowering has been observed to date.

COMPARISON WITH THE PARENT PLANT

Plants of the new cultivar 'OVWOODS01' differs from the parent, an unnamed *Crassula* 'OVCRAS03' (Community Plant Variety Rights grant number 46259), in the following characteristics described in Table 1 below.

TABLE 1

| Characteristic | 'OVWOODS01' | 'OVCRAS03' |
|---|---|---|
| Abundance of foliage. | More abundant. | Less abundant. |
| General coloration of the foliage. | Marbled and striped with a mixture of green, yellow-green and greyed-green; broadly margined white to yellow-white. | Medium green. |
| Foliage luster. | Less glossy than 'OVCRAS03'. | Glossier than 'OVWOODS01'. |
| Foliage margin. | Slightly textured with very small bumps and incisions. | Entire. |

COMPARISON WITH THE CLOSEST KNOWN COMPARATOR

Plants of the new cultivar 'OVWOODS01' differs from the species, *Crassula* 'Crasmada' (U.S. Pat. No. 28,426), in the following characteristics described in Table 2 below.

TABLE 2

| Characteristic | 'OVWOODS01' | 'Crasmada' |
|---|---|---|
| Growth habit. | Less upright. | More upright. |
| Plant size. | Larger than 'Crasmada'. | Smaller than 'OVWOODS01'. |
| Foliage size. | Larger than 'Crasmada'. | Smaller than 'OVWOODS01'. |
| General coloration of the foliage. | Marbled and striped with a mixture of green, yellow-green and greyed-green; broadly margined white to yellow-white. | Dark green. |

That which is claimed is:

1. A new and distinct variety of *Crassula* plant named 'OVWOODS01', substantially as described and illustrated herein.

* * * * *